United States Patent

Gary et al.

[11] Patent Number: 5,160,340
[45] Date of Patent: Nov. 3, 1992

[54] AUTOPSY APPARATUS

[76] Inventors: James A. Gary, 11506 Accolade Ter., Clinton, Md. 20735; Samuel Merrill, Jr., 18624 Hedgegrove Ter., Olney, Md. 20832

[21] Appl. No.: 627,584

[22] Filed: Dec. 14, 1990

Related U.S. Application Data

[62] Division of Ser. No. 207,519, Jun. 16, 1988, abandoned.

[51] Int. Cl.$^5$ ............................................. A61B 17/14
[52] U.S. Cl. .................................. 606/176; 606/172; 606/180; 30/101; 83/881; 83/887
[58] Field of Search ................. 606/82, 172, 176, 177, 606/178, 180; 83/483, 490, 881, 887, 54, 329; 30/101

[56] References Cited

U.S. PATENT DOCUMENTS

| | | | |
|---|---|---|---|
| 436,804 | 9/1890 | Roberts | 606/178 |
| 803,498 | 10/1905 | Masland | 606/176 |
| 962,003 | 6/1910 | Burdick et al. | 83/490 |
| 1,932,462 | 10/1933 | Howlett | 30/101 X |
| 1,942,766 | 1/1934 | Banion | 606/172 X |
| 2,179,250 | 11/1939 | D'Amato | 606/176 |
| 2,291,395 | 7/1942 | Levey | 30/101 X |
| 2,698,621 | 1/1955 | Fernandez | 606/172 |
| 2,842,238 | 7/1958 | Shaw et al. | 30/101 X |
| 4,416,062 | 11/1983 | Cummings | 30/101 |
| 4,461,296 | 7/1984 | Hodge | 606/176 |

FOREIGN PATENT DOCUMENTS

| | | | |
|---|---|---|---|
| 670230 | 11/1929 | France | 606/172 |
| 848002 | 7/1981 | U.S.S.R. | 606/172 |
| 1037909 | 8/1983 | U.S.S.R. | 606/172 |
| 218942 | 7/1924 | United Kingdom | 606/176 |

*Primary Examiner*—Michael H. Thaler
*Attorney, Agent, or Firm*—Glenna Hendricks

[57] ABSTRACT

Method and apparatus for skullcap and other bone cutting during autopsy. A power driven rotary cutter in the form of a circular blade saw is mounted on a carrier which moves around the skull of the cadaver and permits the cutter to move radially, toward and away from the axis of the skull. A follower which engages the skull controls the depth of cut so that only the skull bone is cut without damage to the brain tissue in the skull. The cutter is driven by a cable from a remote motor to minimize the weight of the cutter assembly on the carrier. The casing in which the cutter is mounted can be a handpiece of a cable driven tool. The cutter can also be used manually by removing the handpiece from the carrier. Power to the cutter is controlled so that the cutter cuts only bone and stops when soft tissue is engaged by the cutter, which avoids serious damage to soft tissue, and also avoids serious injury to the user if the blade slips.

14 Claims, 6 Drawing Sheets

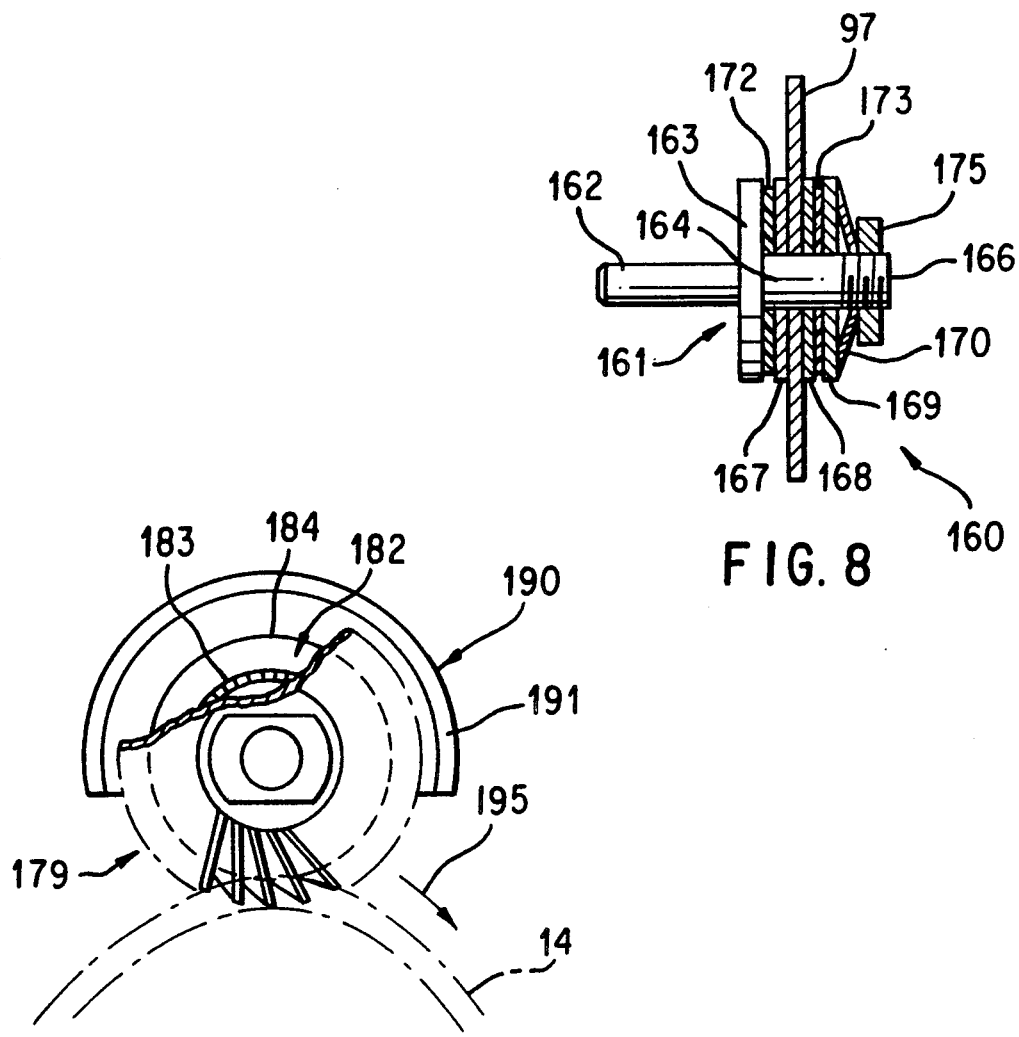
FIG. 8
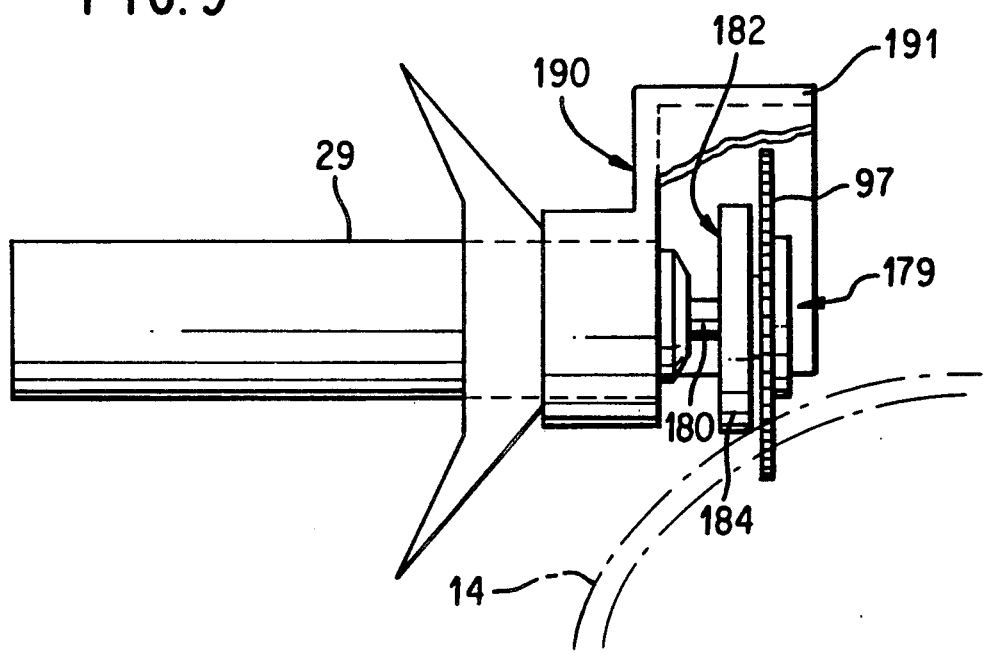
FIG. 9
FIG. 10

AUTOPSY APPARATUS

This is a division of application Ser. No. 207,519, filed Jun. 16, 1988 now abandoned.

The present invention relates to autopsy methods and apparatus for use, for example, in hospitals and in Medical Examiners' offices. In particular, the invention relates to methods and apparatus for cutting bone during an autopsy, such as a skullcap to obtain access to the brain for autopsy examination.

BACKGROUND OF THE INVENTION

Many jurisdictions require an autopsy to be performed to assure that death was from natural or accidental causes, and an autopsy is sometimes requested or permitted by the family of the deceased, even though not legally required. It is not unusual for a Medical Examiners' office, in an urban area, to perform a number of autopsy examinations a day.

Most autopsy examinations require examination of the brain. For examination of the brain, a cut is made around the hollow upper portion of the skull bone, usually slightly above the region of maximum diameter, and the resulting skullcap is lifted and removed to expose the brain for examination and/or removal.

The technician and a pathologist or Medical Examiner usually work together during an autopsy. The technician does the skullcap cutting and the bone cutting necessary to open the chest cavity, to remove the organs for examination.

The know technique for cutting a skullcap is to draw a line around the skull and then cut along the line with an autopsy saw which is a hand held electric motor driven oscillating blade saw, that is alleged to cut bone without cutting adjacent soft tissue. The technician does the skullcap cutting with this saw, usually by cutting around the skull several times until the skull bone is severed to remove the skullcap. Sometimes, the skull is not cut completely through at all locations. When only a thin section or sections of bone remain, a T-blade can be used to break the remaining sections and pry off the skullcap.

Cutting the skullcap in this known manner is time consuming and tedious, because the oscillating blade cuts bone very slowly, and significant pressure is required to cut the bone. The time required to cut the skullcap in this manner is about thirty minutes. Cutting the skullcap requires constant attention, and is uncomfortable for the technician because the part of the autopsy saw gripped by the hand of the technician becomes quite hot, when the autopsy saw is operated for such long periods of time. Further, considerable skill is required to avoid damaging brain tissue, and an unskilled or careless technician can cause cosmetic damage to the head which is difficult for a mortician to repair and conceal.

Since the skullcap is cut while the body is on an autopsy table or at an autopsy station, the table or station is not available for other autopsy work, and the number of autopsy examinations that can be performed at a facility is often limited by the time required for skullcap cutting. It is more significant that the pathologist or medical examiner must often wait for the skullcap to be cut, and it is common practise for a pathologist or Medical Examiner to do only one autopsy at a time, to avoid any possibility of intermixing data or organs of different cadavers. Because of the relatively high overhead factors of such facilities, skullcap cutting and removal at present is quite expensive, and is often the cause of a backlogs for Medical Examiners.

SUMMARY OF THE INVENTION

The method and apparatus of the invention provides for rapid skullcap cutting and removal, and avoids the problems encountered in the past, such as damage to brain tissue and cosmetic damage to the head, and is fast and efficient.

The human skull is not spherical, but is of somewhat irregular oval shape in the region where the skull cap is usually cut. In addition, the skull bone is of non-uniform thickness which varies somewhat around the region where the skull cap is usually cut. While thickness variations are usually found in similar circumferential regions of different skulls, it is quite unusual to find two skulls which are of identical contour and thickness.

In accordance with one aspect of the invention, a powered cutter is used which is mounted on a carrier which guides the cutter around the skull to cut the skull bone in a plane so that the end of the cut perfectly meets the beginning of the cut. While the carrier for the cutter can be revolved around the skull manually, it is preferred that the carrier be motor driven to revolve about the skull to automatically cut around the skullcap.

The cutter is mounted on the carrier to move generally radially toward and away from the axis of the skull as the cutter is moved around the skull to maintain the cutter in a cutting position relative to the skull despite the irregular contour of the skull. During such cutting, the head of the cadaver is held to prevent its movement. For this purpose the apparatus includes means for holding the head of the cadaver in a generally centered position with respect to the path of travel of the cutter around the head.

In one preferred mode of regulating the depth of cut to avoid damage to the brain, in accordance with the invention, a follower in the form of an interior guide finger or guide element is provided which is inserted in an initially formed cut or slit in the skull to engage the inner surface of the hollow skull bone. This finger has a rounded leading portion to enable the finger to move forward between the inner surface of the skull and the outer surface or dura of the brain without damaging brain tissue, as the cutter is advanced to cut the skull bone. At least the portion of the finger which extends through the cut formed by the rotary cutter has a width slightly less than the width of cut made by the cutter.

A preferred cutter is a rotary circular saw blade and at least the portion of the finger which extends through the cut formed by the saw is coplaner with the saw blade and has a width slightly less than the width of cut made by the saw blade. The finger is spaced only slightly outwardly of the periphery of the saw blade, and is secured to the saw casing behind the saw blade, so the finger can move forward, as cutting proceeds. The support portion connecting the finger to the saw casing follows the blade through the cut formed by the blade. A slight outward pressure on the saw as it is moved around the skull maintains the finger against the inside of the skull bone to limit the depth of penetration of the saw blade to cut only to the inner surface of the skull bone. Such outward pressure can be obtained by rotating the blade in the direction of travel of the blade so it tends to climb around the skull, and thereby exerts a component of force outwardly away from the skull. The outward pressure can also be maintained by a spring so that the blade can be rotated in either direction.

Thus, the guide finger guides the peripheral cutting edge of the saw blade precisely along the inner surface of the skull bone, to cut completely through the skull bone in a single pass or revolution about the skull, without damaging the brain tissue located just inwardly of the inner surface of the skull.

It has been found, however, that the thickness of the skull around the periphery where the skullcap is usually cut for autopsy, is sufficiently uniform that a cut of predetermined substantially constant depth relative to the outside surface of the skull, is satisfactory to cut through most portions of the skull while avoiding damage to those portions of the brain which would hinder the post mortem examination. After such a constant depth cut is made, any remaining sections of the skull can be cut by hand, using the conventional oscillating bone saw or the cutter of the invention, or the remining sections can be cracked and the skullcap can be pried off using the T-blade.

It has also been found that the range of thicknesses of different skulls around the periphery where the skullcap is cut is such that most skullcap cutting can be done satisfactorily with only a few different cutting depths.

Another preferred mode of regulating the depth of cut to avoid damage to the brain is to set the maximium depth of cut, for example, with a guide or follower, such as a bushing or roller, that rides on the outside of the skull and limits the depth of cut. In this mode of the invention the depth of cut selected is not greater than about the minimum thickness of the skull along the line of cut to avoid damaging brain tissue. The thicker portions of the skull which are not completely cut, are then cut through by hand with the oscillating autopsy saw, or with a hand manipulated rotary power saw in accordance with another aspect of the invention. When only very thin sections are left, the skullcap can be pried off with the T-blade.

The carrier for revolving the cutter around the skull can be mounted on a wheeled cart or similar moble structure so the apparatus can easily be moved to and clamped or latched to the table, pallet, or gurney used to support the cadaver. The height of the carrier above the floor can be adjusted to permit efficient use with tables or pallets of different heights.

A unique aspect of the invention is that the casing of the cutting head can take the form of a handpiece of a cable driven power tool. The circular blade saw is thus driven from a remotely located motor to minimize the weight and bulk of the cutting head when mounted on the carrier or when used manually. A quick connect arrangement is provided to facilitate mounting the cutting head on the carrier and removing the cutting head from the carrier for manual use.

The cutting head can be used manually to form the initial slit in the skull cap, to receive the guide finger. The cutting head can also be used manually to cut the entire skull cap, without using the carrier. Other autospy bone cutting, such as cutting the breast plate, can also be done by hand with the cutting head.

It has been found, in accordance with another aspect of the invention, that by controlling or limiting the power transmitted to the circular saw blade, the blade can be controlled so it will efficiently cut bone, but will not readily cut soft tissue, and thus, damage to organs with such soft tissue is essentially avoided if the cutter slips while the blade is used manually. This is also a very important safety feature which prevents serious injury to a user who accidently engages the rotating saw blade.

It is correspondingly an object of the invention to provide a method and apparatus for quickly and efficiently cutting a skullcap for removal, and which avoids many of the problems encountered in the past.

It is another object of the invention to provide such an apparatus for automatically and quickly cutting a skullcap with minimal manual assistance.

It is another object to provide such apparatus which is wheeled or mobile, so it is readily movable to the cadaver support table, and which is of adjustable height relative to the floor, so it can easily be used with cadaver support tables of different heights.

It is a further object to provide a powered rotary saw having a depth gauge, wherein the saw can quickly be connected to a carrier for automatic or controlled revolution about the skull, for cutting the skull cap without damaging brain tissue.

It is a further object to provide a powered rotary circular saw having a depth gauge, and which can be used manually for skull cap cutting without damaging brain tissue.

It is a further object to provide apparatus according to one or more of the above objects, in which the depth of cut of the powered rotary saw is regulated by a guide finger which engages the inside surface of the skull to guide the blade to cut only the skull cap without cutting or damaging brain tissue within the skull.

It is another object to provide a power driven saw blade which will efficiently cut bone, but which is controlled to stop cutting upon engagement of soft tissue so that soft tissue organs are not damaged, and servious injury to the user is avoided.

These and other objects and advantages are attained in accordance with one aspect of the invention, by providing, a cradle within or adjacent which the head or skull is positioned and retained, a carrier on which the rotary cutter is supported to move around the periphery of the skull, and follower or guide means engaging the skull, to enable the rotary saw to move inwardly and outwardly relative to the longitudinal axis of the skull to thus control the extent of inward penetration of the cutter into the skull to cut around the skull while avoiding damage to the brain.

In accordance with the invention, the cradle can take the form of a support frame or ring with skull positioning elements such as adjustable pins or clamp screws for supporting and fixing the skull in the cradle.

The carrier can take the form of a ring rotatable on the cradle, and which includes a cutter support which enables the cutter to move toward and away from the axis of the skull as it moves around the skull, and a follower associated with the cutter or its support and which engages the skull to control the cutter to cut the skull bone without damage to the brain.

In accordance with another aspect of the invention the circular saw cutter can be used manually to cut the skull cap, as well as other bones, such as the breastplate, which require cutting for autopsy purposes. By controlling the power transmitted to the circular saw blade, severe damage to soft tissue organs and severe injury to the user is avoided, in the event of accidental engagement with the blade, while bone is cut efficiently.

Other features and advantages will become apparant from the drawings and the description which follows.

BRIEF DESCRIPTION OF THE DRAWINGS

FIG. 8 is a view in section of a slip clutch for controlling the power supplied to the cutter blade;

FIG. 9 is a front end view of a second embodiment of cutter and follower, according to the invention, which can be used with the automatic apparatus of FIGS. 1-5, and can also be used manually, and FIG. 10 is a side view of the cutter and follower of FIG. 9.

DETAILED DESCRIPTION

Figure 1:
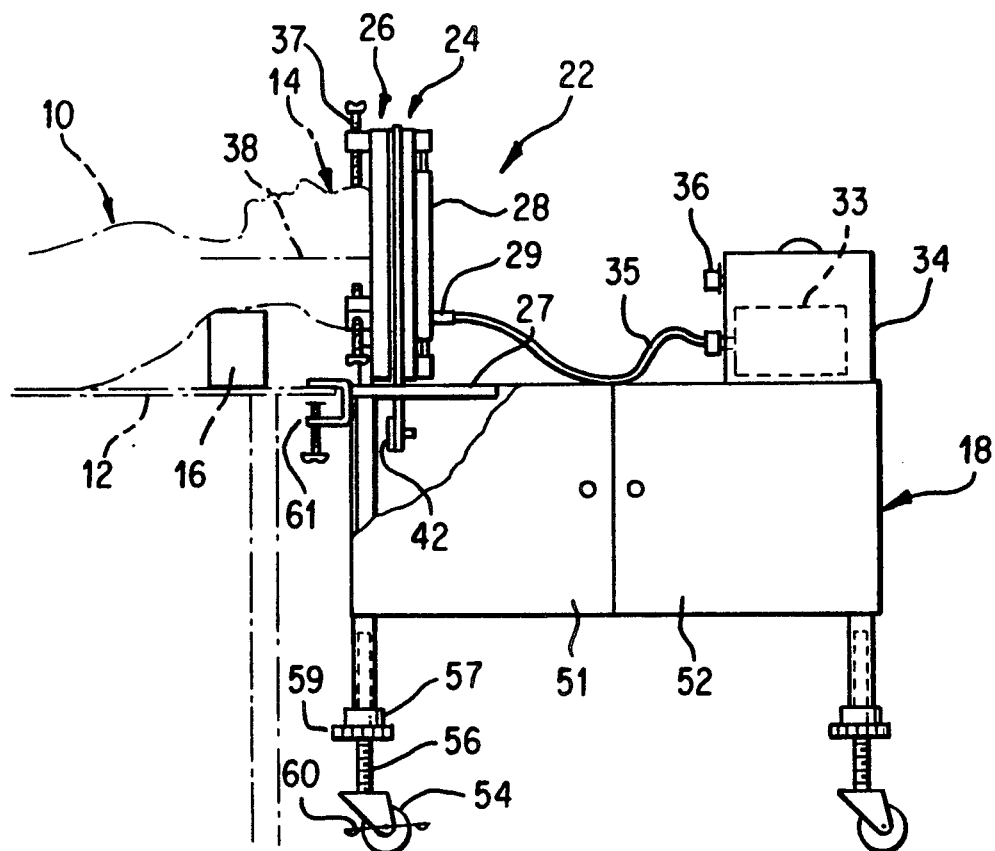
FIG. 1 is somewhat schematic side view of an embodiment of an apparatus according to the invention for automatical cutting a skull cap of cadaver shown in phantom lines.

As shown schematically at FIG. 1, during an autopsy, the cadaver 10 (partially shown in phantom lines) is placed face up on a gurney or table 12, with the head or skull 14 of the cadaver at the end of the table 12, and a block or support 16 is often placed under the neck or shoulders of the cadaver to lift and support the head 14.

Figure 2:
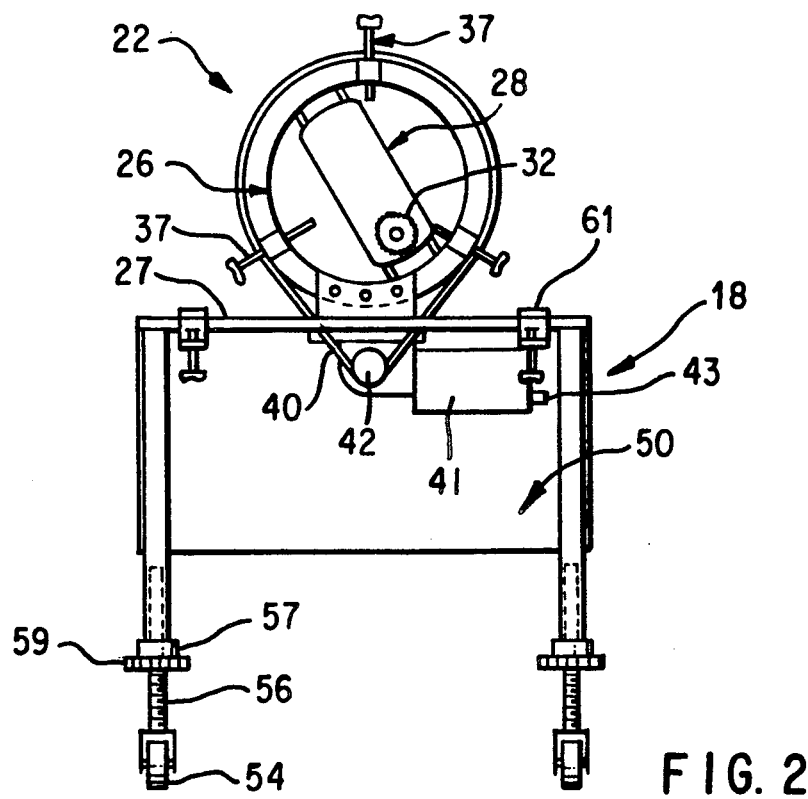
FIG. 2 is a front view of the apparatus of FIG. 1.

As shown at FIGS. 1 and 2, one embodiment of the invention includes a table or cart 18 with a skull cap cutting apparatus 22 mounted thereon.

Skull cap cutting apparatus 22 includes an annular carrier assembly 24 mounted for rotation on the rear of a stationary support ring or cradle assembly 26. The support ring is secured to the top 27 of cart 18 with the axis of the ring horizontal, and the carrier assembly rotates about a horizontal axis. A radially moveable slide or shuttle assembly 28 is mounted on the rear of the rotatable carrier assembly 24.

As shown at FIG. 1, an elongated casing 29 containing a rotatable spindle is mounted near one end of slide assembly 28. The casing 29 extends horizontally through and is secured to the slide assembly. A rotary cutter 32 is mounted on the spindle as shown at FIG. 2. The cutter is driven by a variable speed motor 33 contained in a protective portable housing 34. Motor 33 is mechanically connected to the spindle in casing 29 by an elongated flexible shaft drive cable 35. A motor speed control knob 36 is on the front of housing 34, and the speed control circuitry is within the housing. The casing 29 can be the handpiece or handle of a cable drive tool.

Circumferential spaced radially extending positioning pins 37 are threaded through blocks mounted on the front face of support ring assembly 26 and can be manually adjusted to position and hold the head of the cadaver generally centered during cutting of the skull cap. FIG. 1 shows the head 14 positioned so that its longitudinal axis 38 is horizontal.

The carrier assembly 24 is driven with a V-belt 40 from a variable speed reduction gear electric motor 41 to revolve the carrier assembly 24 around the head 14 of the cadaver. Motor 41 is mounted on the underside of top 14, has a V drive pulley 42 on its output shaft, and a speed control knob 43. The mounting for the motor can be an adjustable mount to adjust the tension in belt 40.

The cart 18, as shown at FIGS. 1 and 2, has portions of its side panels and front panel removed to better show the compartment 50 in which motor 41 is located, and which provides a storage area in which accessories, such as cutter blades, and the housing 34 containing motor 33 can be stored when not in use. For this purpose, hinged doors 51, 52 can be provided on each side of the cart 18.

Cart 18 has lockable caster wheels 54, each on adjustable legs 56, so the height of the top of the cart and thus the skull cutting appartus 22 mounted thereon can be adjusted vertically to facilitate use with cadaver support tables 12 of different heights. As shown, each leg 56 has an externally threaded section which threads into a threaded sleeve 57 fixed to the lower end of a tube at each corner of the cart. A threaded lock-nut ring 59 on each leg is adapted to be rotated manually to abut the bottom end of a sleeve 57 to lock each leg in its adjusted position.

To maintain the cart in position adjacent the end of table 12, the wheel locking levers 60 can be operated In addition, clamps 61 at front of the cart can be used to clamp the cart to the table 12, as shown at FIG. 1.

Figure 3:
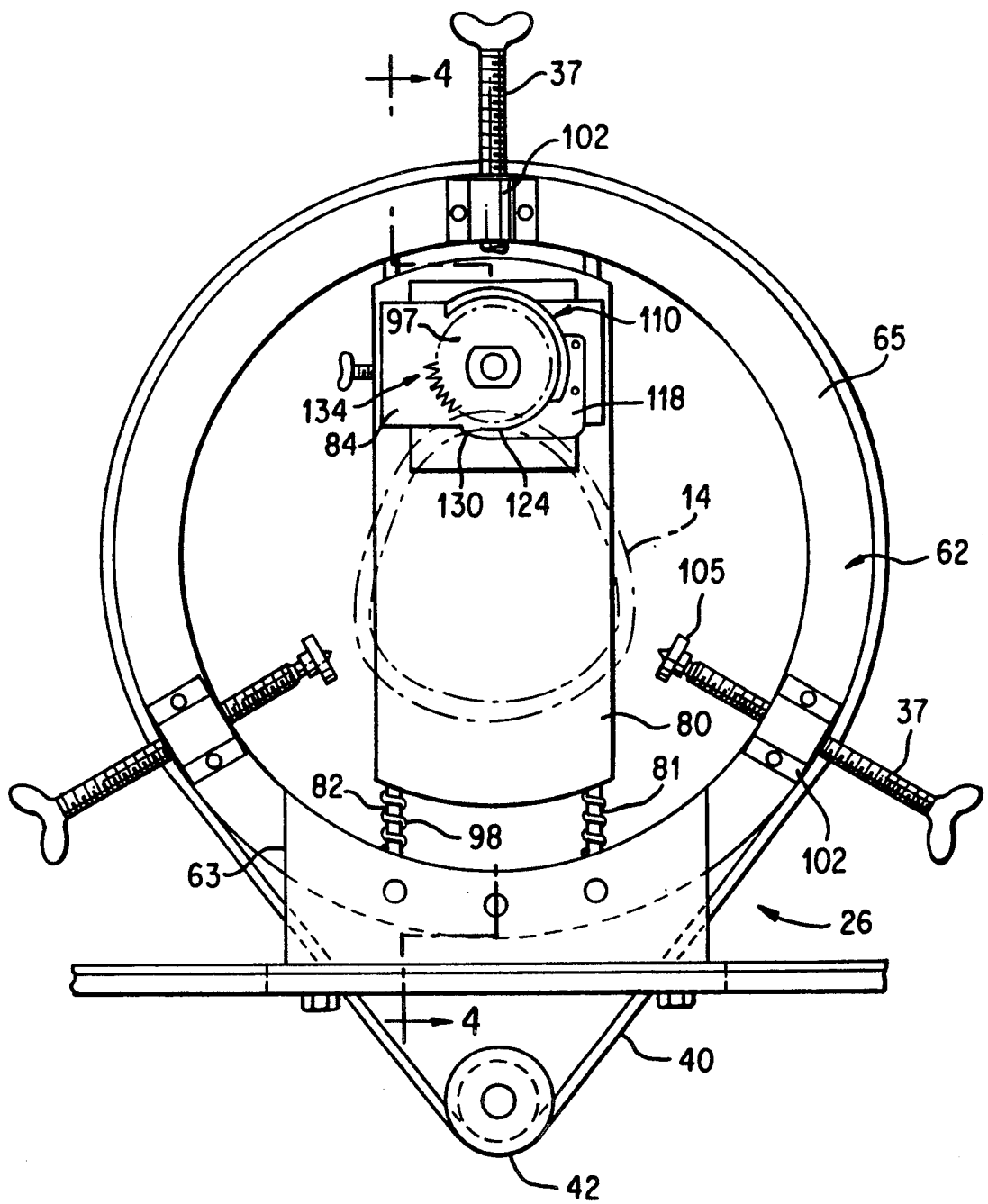
FIG. 3 is an enlarged front view of the cutter carrier and its cradle support, and shows the position of the cutter during cutting of a skull cap using one form of follower according to the invention.
Figure 4:
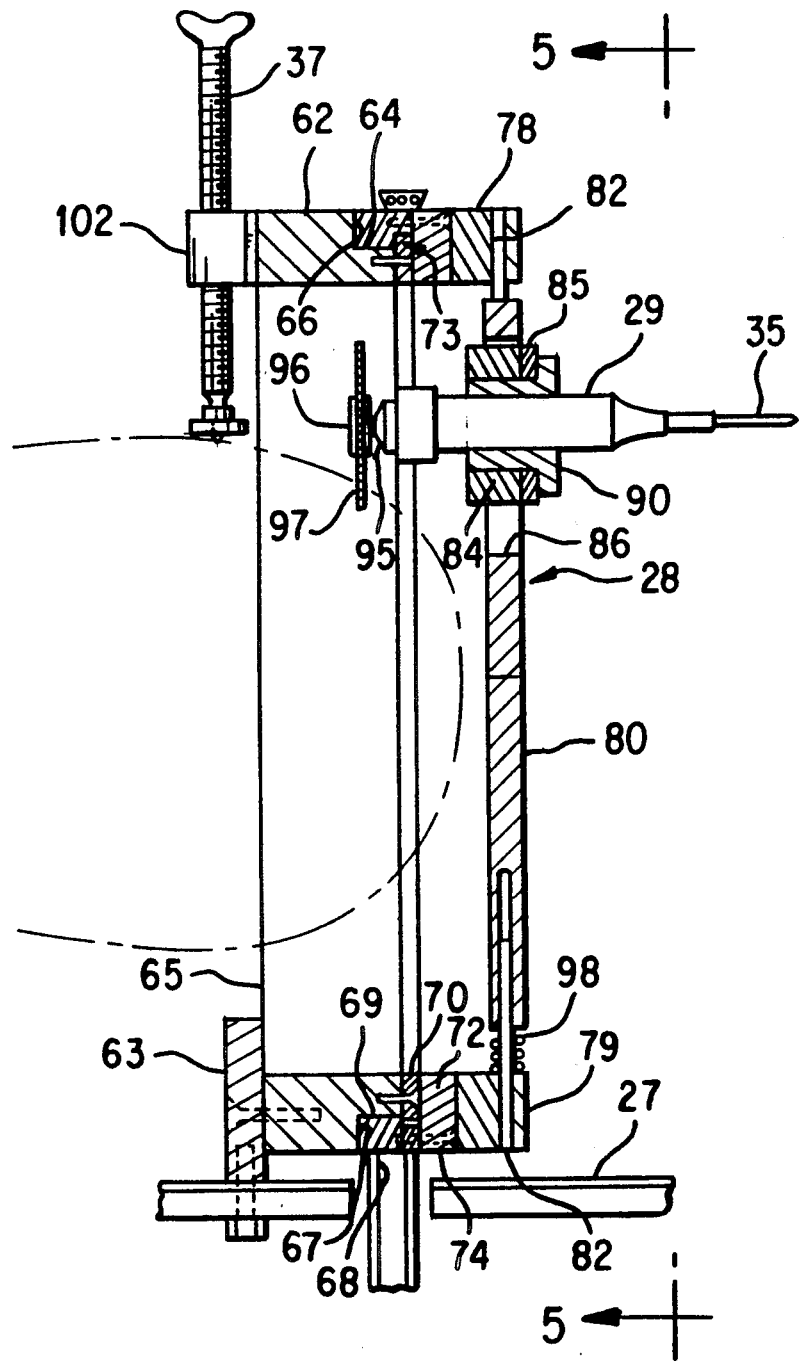
FIG. 4 is a view in section looking along line 4—4 of FIG. 3.
Figure 5:
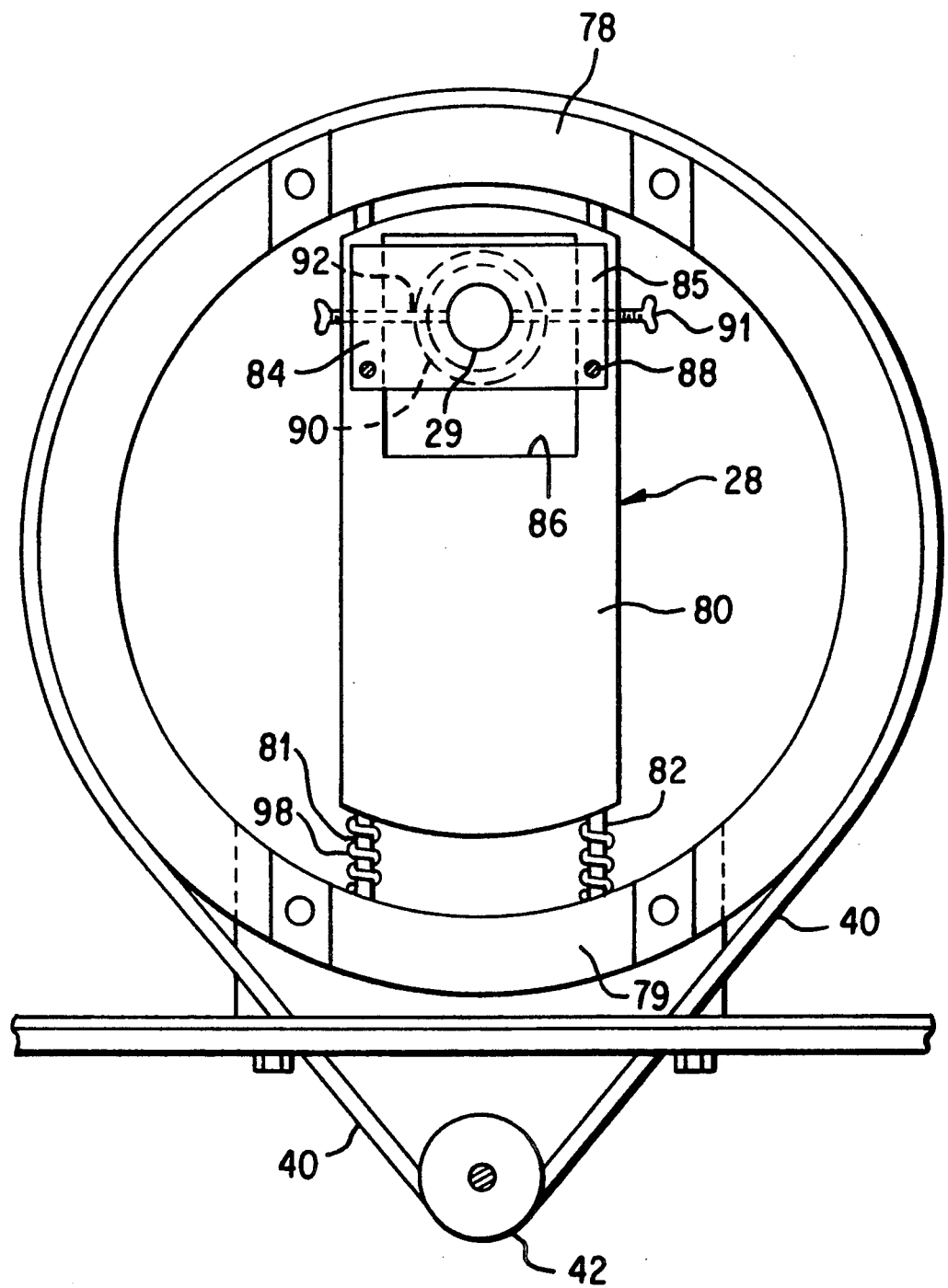
FIG. 5 is a rear view of the cutter carrier looking along line 5—5 of FIG. 4.

As shown as FIGS. 3, 4, and 5, support assembly 26 includes a support ring 62 fixed to the reinforcing plate of the top 27 of the cart 18 by a mounting block 63, so the ring 62 is supported in cantilever fashion from its front face 65. Support ring 62 is L shaped in section, as shown at FIG. 4, to provide an external cylindrical journal surface 64 and a flat annular rearwardly facing shoulder 66.

The carrier assembly includes a bearing ring 68, having an annular end face 67 and an internal cylindrical bearing surface 69. Bearing ring 68 is mounted for rotation on journal surface 64, and is held against axial movement by a retaining ring 70 which acts as a thrust bearing and extends across an annular bearing shoulder 72 of an interior recess 73 of bearing ring 68. Retaining ring 70 is fixed to the rear face of support ring 62 with screws which are recessed in the rear face of the retaining ring. A carrier ring 74 seats on the rear face of bearing ring 68, and is secured to the bearing ring with screws. The thickness of retaining ring 70 is only slightly less than the axial width of the recess 73 in bearing ring 68, and the length of bearing surface 69 is only very slightly less than the length of journal surface 64, to provide a bearing arrangement resistant to entry of bone dust and liquids.

Thus, support ring 62 and retaining ring 70 are fixed and stationary, and the carrier assembly 24 comprised of bearing ring 68, carrier ring 74, and the slide assembly 28, can revolve as a unit on the support ring. The bearing ring 68 has a smooth outer surface which is engaged by the flat inner surface of the the V drive belt 40 to rotate this carrier assembly when the reduction gear drive motor 41 is energized.

Diametrically opposed carrier blocks 78, 79 (FIGS. 4 and 5), are mounted on the rear face of carrier ring 74. Slide assembly 28 includes a slide plate 80 supported by the blocks 78, 79 for movement radially of the carrier ring 74. Pairs of parallel guide pins 81, 82 are fixed in the respective carrier blocks 78, 79, so that the axes of the opposed pins are aligned transversely of the carrier ring 74. Parallel bores in each end of the slide plate 80 receive the guide pins 81, 82 to mount the slide plate for movement radially of carrier ring 74.

A cutter support block 84 is mounted on slide plate 80 in a slot 86 formed in and offset toward one end of the slide plate. The block 84 has T shaped block portion, and a retaining plate 85 which holds the T block in the slot. The slot 86 is longer than the block 84 to allow the block to be moved to different positions on the slide plate, to adjust the radial position of the cutter. The block 84 can be clamped with the set screws 88 shown at FIG. 5.

Seated in the cutter support block 84, is a cutter support bushing 90 which is retained with a wing screw 91 (FIG. 5). Bushing 90 has a central opening to receive the casing or handpiece 29, and a thumb screw 92 to lock the handpiece in the bushing. Handpiece 29 has a chuck 95 to receive and grip the shaft of the arbor 96 on which the rotary cutter, in the form of a circular blade saw 97, is mounted. In the embodiment shown at FIGS. 3 to 5, compression springs 98 are mounted on the guide pins 81, 82, between the carrier block 79 and the adjacent end of slide plate 80, to urge the slide plate toward the opposite carrier block 78, for a purpose which will soon be evident.

The cadaver head positioning pins 37 are shown in greater detail at FIGS. 3 and 4. These pins extend through respective support blocks 102 fastened to and projecting from the front face of support ring 62. The pins 37 each take the form of a thumbscrew, with a pad 105 swivel mounted at the inner end of the screw and having a pointed tip for secure non-slip engagement with the head or skull of the cadaver.

The handpiece 29 is a conventional cable driven handpiece with a quick disconnect cable coupling with the flexible drive cable 35, of the type which enables the handpiece to swivel or turn relative to the cable sheath. The cable sheath is secured to the motor 33 in housing 34 so that the sheath cannot rotate. This enables the carrier assembly to revolve while the cutter is driven, without twisting the cable sheath.

Figure 6:
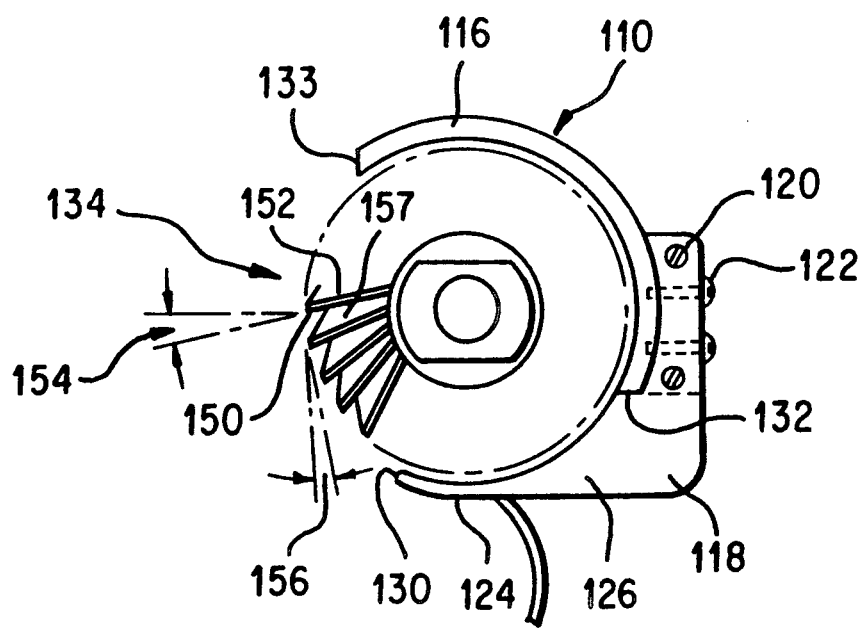
FIG. 6 an enlarged front end view of the cutter, follower, and handpiece used with the automatic apparatus of FIGS. 1-5, and which can also be used manually.
Figure 7:
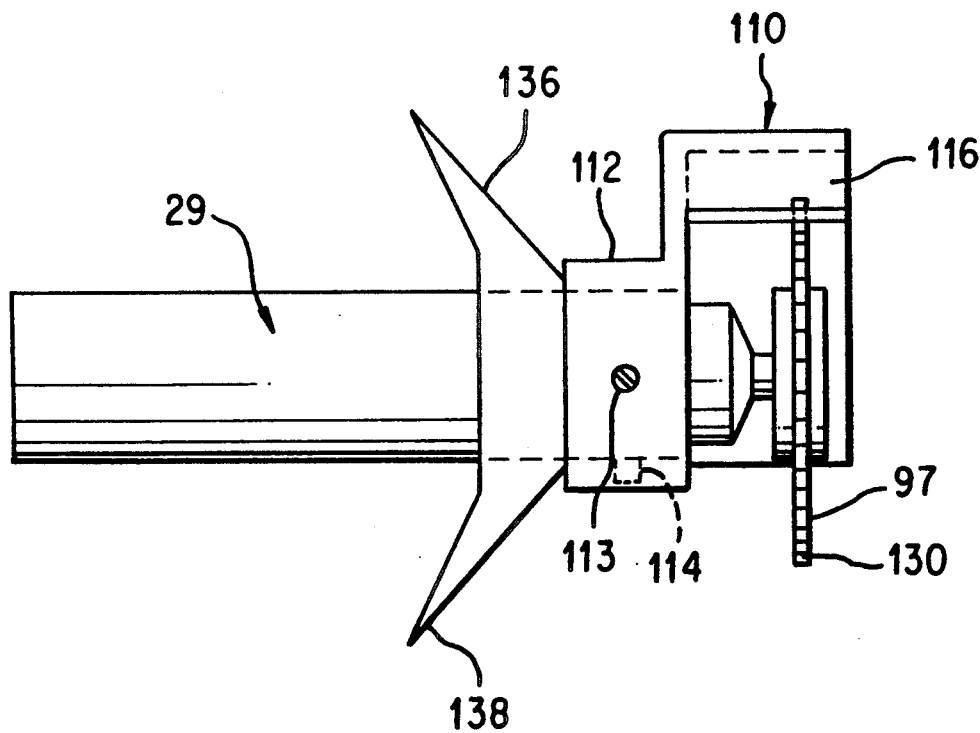
FIG. 7 is a side view of the cutter and handpiece of FIG. 6.

FIGS. 6 and 7 show the handpiece 29 and circular saw blade in greater detail. The handpiece can be used with the skull cutting apparatus of FIGS. 1-5, as well as manually for skull cap cutting and other autopsy bone cutting.

Attached to the handpiece 29 is a blade guard 110. The blade guard has a sleeve portion 112 which is positioned on the cutter end of the handpiece and secured with set screws 113, 114. Blade guard 110 has an integral hood 116 which extends over and partially around saw blade 97. Fixed to the outside of hood 116 is a follower finger plate 118 which is precisely coplaner with blade 97 and extends along and is spaced only slightly outwardly of the periphery of the blade 97. The finger plate 118 is secured by screws 120 to a block secured to the hood by screws 122. The finger plate has a leading follower finger 124 preferrably of a thickness slightly less than the width of cut formed by the saw blade 97, so it can be inserted through an initial cut formed by the blade to engage the inside surface of the skull bone. A connecting portion 126 which connects the finger 124 to the mounting portion 128 is of a thickness less than the width of cut formed by the saw blade 97 so it can move through and in the slit or cut formed by the blade as a cut advances.

The finger 124 has a rounded leading end 130, which engages the dura so that the dura is depressed and not cut by the cutter even if the cutter slips while manually cutting the skull bone, or other bone such as the breast plate.

The blade guard 110 partly encircles the blade 97 to contain bone dust formed during cutting and to shield the blade against accidental contact by the user to avoid injury. The hood 116 of blade guard 110, as measured between the end edges 132 and 133, extends not more than about 180 degrees around the blade, and the finger plate extends about 75 degrees beyond the edge 132 of the hood so that the blade can cut in the region 134 without interference by the finger plate 118 or the hood 116.

When used manually for bone cutting, a circular hand guard 136 is placed on the handpiece 29 so it abuts against the sleeve portion 112 of the blade guard 110, as shown at FIG. 10. The hand guard 136 is of flexible material and has a funnel shaped peripheral skirt 138 which prevents the hand of the person holding the handpiece from slipping toward the blade 97.

The operation of the embodiment described in FIGS. 1-5 will now be explained. First, the cart 18 is moved to the end of autopsy table 12, and the height of the cart is adjusted, if necessary, to the height of the table, by adjusting the legs 56. The cadaver is positioned on the autopsy table 12 with the skull 14 centered on the table, and elevated by the block 16. The line of cut is marked on the skull and cadaver is positioned so this line of cut is a few inches beyond the end of table 12. With thumbscrew pins 37 withdrawn, the cart is moved toward the table so the head 14 of the cadaver enters the assembly 22, and saw blade 97 is in the radial plane of the line of cut on the skull. The clamps 61 on the cart are tightened to secure the cart to the table, and the wheels of the cart can be locked. The thumbscrew pins 37 are then adjusted to position and clamp the skull. The axial position of the saw blade 97 can be adjusted if necessary by loosening thumbscrew 92 (FIG. 5) and sliding the handpiece 29 axially in the bushing 90, so the blade is exactly at the desired line of cut of the skull, and thumbscrew 92 is then slightly tightened.

The handpiece 29 is then rotated counterclockwise (as viewed in FIG. 3) from the cutting position show at FIG. 3, until the exposed portion 134 of the blade 97 faces the skull, and thumbscrew 92 is then tightened. Then, cutter drive motor 33 is energized to rotate the saw blade 97, and the slide plate 80 or the rear of handpiece 29 is grasped to push the rotating blade toward and into the skull against the action of the weak compression springs 98, to form an initial or starting slit in the skull. Then, the handpiece thumbscrew is loosened, the handpiece is turned in the block to the position shown at FIG. 3 in which the finger 124 extends through the starting slit and the end 130 of the finger engages the interior of the skull bone at a position slightly ahead of the blade 97, and thumbscrew 92 is tightened to lock the handpiece in this position. The engagement of the end 130 of the finger with the interior of the skull prevents the springs 98 from pushing the slide and cutter away from the skull.

The carrier drive motor 41 is then energized to revolve the carrier assembly and saw blade 97 counterclockwise around the skull, as viewed at FIG. 3. The blade 97 is also rotated counter clockwise. As thicker portions of the skull are engaged by the finger, the saw blade is pulled further inwardly into the skull to cut through all portions of the skull bone in a single revolution of the carrier assembly 24. The finger causes the slide plate 80 to move radially relative to the longitudinal axis of the skull which in turns moves the blade 97 radially to follow the interior contour of the skull. The rounded end 130 of the finger depresses any portions of the dura which it engages, so this covering of the brain is not engaged or cut by the saw blade. The speed of revolution of the carrier assembly and blade around the skull is about one revolution in two to four minutes, and the cut cap is thus quickly cut. The cut formed around the skull is clean and coplaner and avoids any cosmetic damage to the skull.

The thumbscrews 37 are then released from the skull, clamps 61 are released, and the cart is moved away from the table 12.

Because of the quick disconnect coupling, the cable 35 can quickly be disconnected from the handpiece 29, and the handpiece can be removed from the apparatus 22 by loosening the thumbscrew 92 and withdrawing the handpiece and cutter as an assembly, forwardly through the support ring 62, for manual cutting of bone, such as the breastplate of the cadaver. An additional handpiece and cutter can be provided so it is not necessary to remove the handpiece 29 from the apparatus 22 for manual cutting.

The cutter with guide finger can be used manually to cut the skull cap for removal, or to cut other bones which need to be cut during an autopsy. The skull cap is cut manually by first orienting the handpiece to cut into the skull with the exposed portion 134 of the blade between the end 130 of the finger and the edge 133 of the hood, and the handpiece is then turned so the finger enters the cut and engages the inside surface of the skull. The blade is then moved manually around the skull to sever the skull cap in a single pass around the skull.

To assist maintaining the finger in engagement with the interior of the skull, when used manually or with the automatic apparatus 22, the saw blade is rotated to cut from the outside of the skull toward the inside so that the blade tends to climb along the outside of the skull thus exerting an outward force on the cutter which tends to pull the finger 124 into engagement with the inside surface of the skull, or other bones during cutting. The direction of rotation is is thus toward the free end 130 of the finger, counterclockwise as viewed from the blade end, when the finger extends clockwise from the guard.

FIG. 6 shows a preferred circular saw blade 97 used for skull cap cutting, and which can also be used for other required bone cutting during an autopsy. Blade 97 is a circular blade with both peripheral teeth 150 and side cutting teeth 152 (on each side of the blade). The periphiperal teeth have a positive radial relief angle 154 (the angle between the cutting edge of a tooth and the radius of the blade) which can be in the range of 5 to 30 degrees, and a radial relief angle or tooth clearance angle 156 which can be in the range of about 5 to 15 degrees. The side teeth have axial relief, and the flutes 157 taper inwardly toward the next following tooth. Such a blade has been found to cut the skull bone easily and without binding. A preferred saw blade 97 is a metal slitting saw of stainless steel with 28 teeth, is 2½ inches in diameter, and has a thickness of ⅛ inch.

It has been found, surprisingly, that the saw blade 97, when driven with a relatively low power drive motor 33, in the range of about ⅛ to 1/6 horsepower, will not readily cut soft tissue, and thus, damage to organs with such soft tissue is essentially avoided if the cutter slips. When the cutter engages such soft tissue the drive motor stalls and the tissue is not cut. Such stalling of the drive motor when the cutter engages soft tissue serves also as a safety feature to prevent serious injury to a user who accidently engages the rotating saw blade.

FIG. 8 shows another means for controlling the torque supplied to the blade 97, in the form of a slip clutch 160. Slip clutch arrangement 160 limits the power transmitted to the blade to avoid cutting soft tissue and to avoid serious injury to the user.

As shown, blade 97 is mounted on an arbor 161 having a shaft 162 adapted to be chucked in the collet of the handpiece 29. Arbor 161 has an integral collar 163 with a smooth end face, and a smooth journal surface 164 with a thread 166 at its free end. Washers 167, 168, are disposed on opposite sides of blade 97 and can be keyed to the blade.

Mounted on the free end of journal 164 is a pressure plate washer 169, a belleville spring 170, and a threaded ring 171. A low friction slip disk 172 is between collar 163 and washer 167, and a slip disk 173 is between pressure plate 169 and washer 168. The respective surfaces of collar 163 and washer 167 which engage disk 172 are smooth and polished, as are the surfaces of washer 168 and pressure plate 169 which engage the disk 173. This assembly forms an adjustable slip clutch which enables the assembly of blade 97 and washers 167, 168, to slip and stall if overloaded, while arbor 164 continues to rotate.

The ring 173, when advanced on thread 166, compresses the belleville spring to axially load the clutch. The ring is adjusted until the blade slips at the predetermined torque necessary to cut bone without cutting or badly damaging soft tissue. The low friction slip disks 172, 173 can be thin disks of TEFLON, and the ring 173 can have a self locking thread to retain its adjusted position or the thread 166 can be a self locking thread.

FIGS. 9 and 10 show a second embodiment of depth gauge and cutter assembly 179, in accordance with the invention, which can be used with the automatic apparatus of FIGS. 1-5, as well as manually for autopsy bone cutting. Mounted on a saw arbor 180 between the blade 97 and the handpiece 29 is a depth gauge bushing 182 which limits the depth of cut of the saw blade 97. The bushing 182 has ball bearings 183 so its outer peripheral portion 184 is freely rotatable relative to the blade and the arbor 180. Thus, the outer portion 184 can roll on the skull or body, or remain motionless, when the arbor and blade are rotated.

The blade guard 190 (FIG. 9) in this embodiment has a hood 191 which extends somewhat more than 180 degrees around the blade 97, and there is no finger plate 118.

When used manually for skull or bone cutting, a cutter assembly 179 is selected which has a bushing 182 which limits the depth of cut to, for example, 3/8 inch. The line of cut is drawn on the skull, and the rotating blade 97 is engaged with the skull 14 to cut into the skull until the outer portion 184 of the bushing engages the skull 14, as shown at FIGS. 9 and 10. The blade is then moved around the skull while inward pressure is exerted to maintain the bushing against the skull and form a cut of uniform depth around the skull. Only slight inward pressure is required if the blade 97 is moved around the skull in a direction opposite to the direction of rotation of the blade, in the direction of the arrow 195 in FIG. 9. The inside-out cutting action of the blade 97 tends to pull the blade toward the skull or other bone being cut. The bushing rolls on the skull as the skull cap is cut.

After the cut is made there may be some thicker uncut portions of the skull which require cutting or separation to remove the skull cap. If these sections are not too thick they can be separated with the usual T bar. If further cutting is necessary, it is preferred to have a second handpiece fitted with a thinner blade (without a depth bushing) to perform the further cutting manually, or this thinner cutter without a bushing can be chucked in the handpiece.

For the embodiment of FIGS. 9 and 10, several cutter assemblies 179 are provided, each with a different diameter depth bushing, so the user need only select the assembly which provides the desired depth of cut of, for example, ¼ inch, 5/16 inch, ⅜ inch, 7/16 inch, or even ½ inch for a very thick skull. A cutter assembly is also provided without a bushing for cutting through thicker sections of skull and for general autopsy bone cutting.

Use of the cutter assembly of FIGS. 9 and 10 with the automatic apparatus of FIGS. 1 to 5 requires slight modification of the apparatus, for most efficient use. First, the springs 98 (FIGS. 4 and 5), are removed from the pins 81 and 82 at one side of the carrier ring 78, and are placed on the pins 81 and 82 at the opposite side of the carrier ring, between slide 26 and carrier block 78, so that the slide, and cutter support block 84 and handpiece 29 on the slide are urged toward the skull 14. Also, the direction of rotation of the carrier ring drive motor 41 is reversed, so the ring is driven clockwise (as viewed in FIGS. 2 and 3), while the blade 97 rotates counterclockwise, so that the blade cuts the skull from inside to out, and tends to pull the depth gauge bushing 182 against the outside surface of the skull, to assist the action of the (reversed) springs 98.

The operation of the apparatus of FIGS. 1-5 with the cutter assembly of FIGS. 9 and 10, is then the same as previously described, but a cut of uniform depth is made around the skull, as measured from the outside suface of the skull, and there may be remaining sections of the skull which require separation with the T-bar, or require manual cutting, to remove the skull cap.

Of course, a limited power cutter drive motor 33, or a slip clutch 160 is used with the embodiment of FIGS. 9 and 10, to avoid damage to soft tissue and serious injury to the user.

While preferred embodiments have been shown and described, variations and changes can be made without departing from the scope of the invention. For example, while a limited power motor or a torque limiting clutch are disclosed to avoid accidental damage to soft tissue, or serious injury to the user, any other torque limiting or controlling arrangement can be used instead, to control the power transmitted to the blade or to stop or brake the blade, in response to a predetermined loading of the blade.

Other changes can be made without departing from the scope of the invention.

We claim:

1. An apparatus comprising:
   a circular stationary support;
   a carrier assembly which is mounted on the stationary support;
   a slide assembly which is mounted on said carrier assembly on the surface opposite said stationary support and which is positioned across an opening defined by said stationary support;
   a cutter support block supporting a spindle, said spindle having mounted thereon a circular notary cutter, wherein said cutter support block is movably mounted on said slide assembly with said spindle carrying said rotary cutter extending through a slot in said slide assembly.

2. An apparatus of claim 1 wherein the rotary cutter is driven by a variable speed motor.

3. An apparatus of claim 2 wherein the motor is connected to the spindle by a flexible shaft drive cable.

4. An apparatus of claim 3 wherein the drive cable is encased within a sheath and wherein a swivel connects said sheath to said casing so that said casing can turn without twisting said sheath.

5. An apparatus of claim 4 wherein the drive cable has a quick connect and release connector means for connecting said drive cable to said spindle.

6. An apparatus of claim 1 having radially extending pins mounted on said stationary support to provide support for an object to be cut with the rotary cutter.

7. An apparatus of claim 6 wherein each pin has a screw portion and a swivel pad mounted near the end of each said pin, each said pad having a pointed tip.

8. An apparatus of claim 7 wherein the pins are thumb screws.

9. An apparatus of claim 1 for removing a skull cap from a skull having a following for engaging the skull, said follower having a finger which travels under the skull to limit penetration of the rotary cutter.

10. An apparatus of claim 9 wherein the cutter is a circular saw blade.

11. An apparatus of claim 1 wherein the cutter is a circular saw blade.

12. An apparatus of claim 1 wherein the slide assembly is movably mounted on the carrier by pins.

13. An apparatus of claim 12 wherein the pins holding the slide assembly are surrounded by springs to control the movement of the slide plate.

14. An apparatus of claim 1 wherein the circular support is mounted on a portable frame adapted for attachment to a horizontal surface.

* * * * *